(12) United States Patent
Cooper

(10) Patent No.: US 8,268,241 B1
(45) Date of Patent: Sep. 18, 2012

(54) ACCELERATED OUTGASSING VIA VACUUM/HEAT PROCESS

(76) Inventor: Henry W. Cooper, Marsing, ID (US)

( * ) Notice: Subject to any disclaimer, the term of this patent is extended or adjusted under 35 U.S.C. 154(b) by 444 days.

(21) Appl. No.: 12/287,733

(22) Filed: Oct. 14, 2008

(51) Int. Cl.
*A61L 2/20* (2006.01)

(52) U.S. Cl. ............... 422/33; 422/34; 422/35; 422/65; 422/67; 436/180

(58) Field of Classification Search ............. 422/33–35, 422/65, 67; 436/180
See application file for complete search history.

(56) References Cited

U.S. PATENT DOCUMENTS 5,521,381 A * 5/1996 Gregg et al. ............... 250/288

* cited by examiner

*Primary Examiner* — Jyoti Nagpaul

(57) ABSTRACT

A process wherein outgassing rates of volatile organic compounds (VOCs) in an object, particularly habitable vehicles, are accelerated by placing the subject object in a vacuum chamber and placing heat sources either inside the object being treated, outside the object, or both. The process includes measuring and monitoring the temperature of selected surfaces inside the object being treated. The heat sources are adjusted to maintain a temperature which is safe for the materials and which will promote maximum outgassing rates. During the treatment process, while a vacuum and heat are being applied to the subject object, the gasses in the chamber are monitored for both their composition and quantity. When the outgassing rates of the VOCs reach acceptable levels, the process cycle is terminated. The vacuum in the chamber is broken to restore atmospheric pressure, and the object being treated is removed from the chamber.

6 Claims, No Drawings

ACCELERATED OUTGASSING VIA VACUUM/HEAT PROCESS

BACKGROUND OF THE INVENTION

1. Field of the Invention

The present invention relates generally to outgassing of volatile organic compounds (VOCs), and more particularly is a method of accelerating the outgassing, specifically in vehicles or trailers, via application of a vacuum and heat.

2. Description of the Prior Art

The problems caused by volatile organic compounds (VOCs) in trailers is very much present in the public eye presently given the recent issues of contamination making FEMA trailers uninhabitable and unusable. The problem for the FEMA trailers, and of course other vehicles and trailers as well, is the presence of formaldehyde. Formaldehyde is a common example of a VOC that can be dangerous to humans. Formaldehyde is a colorless gas compound (HCHO) that can irritate eyes, mucous membranes, and the upper respiratory system. It can be inhaled or absorbed by the skin.

However, because formaldehyde is an excellent resin and binding agent and is very inexpensive to produce, formaldehyde is produced in large quantities (approximately 6 billion pounds each year), and is widely used in building materials— especially glue, Urea-formaldehyde foam insulation, and pressed-wood products such as plywood, particle board, paneling and wood finishes. Many floor coverings such as carpet, padding, and adhesives also contain formaldehyde.

The presence of formaldehyde in so many building products makes newly manufactured mobile homes, motor homes, and travel trailers particularly susceptible to high amounts of formaldehyde since so many of the vehicles' components may be made from particle board or pressed-wood products containing formaldehyde. The potentially dangerously high concentrations of formaldehyde in these vehicles are "the cumulative effect of too much formaldehyde-emitting material in too small a space with insufficient ventilation, even though construction materials individually meet standards generally used in the building industry," says Michael McGeehin, PhD, MSPH, Director, Division of Environmental Hazards and Health Effects, Centers for Disease Control and Prevention (CDC), U.S. Department of Health and Human Services, in *Testimony before the Committee on Oversight and Government Reform, U.S. House of Representatives*, 9 Jul. 2008.

The formaldehyde in the trailers enters the ambient air naturally through"outgassing", the natural movement of adsorbed or occluded gasses from a solid to the atmosphere. Because the wall construction material in trailers contains a higher ratio of formaldehyde than standard drywall, and because the ratio of wall, ceiling, and floor areas to enclosed space is higher than in a regular home, HCHO gas levels can be much higher in travel trailers than in stationary construction.

One solution to the problem of dangerous levels of VOCs is to simply leave the trailer unused for a sufficient length of time for ventilation to naturally reduce the concentration of VOCs. This method is inherently disadvantageous due to the inability to use the trailer during the "airing out" period.

Another solution, used particularly in hot weather when high temperature and high humidity raise the outgassing rate, and during the rainy season when people spend more time inside exposed to the formaldehyde gas, is to increase the ventilation in an occupied trailer. One obvious shortcoming of this method is that greater ventilation requires more energy to cool and dehumidify the air. Moreover, increased cooling and dehumidifying can lead to an accumulation of water from condenser coils in refrigerators, swamp coolers, air conditioners, and dehumidifiers, creating a major source of mold. Many authorities suggest that mold and bacteria associated with standing water and increased humidity can cause serious health problems for trailer residents.

Accordingly, it is an object of the present invention to provide a process to accelerate the outgassing process so as to render a subject vehicle habitable without the significant delay required for natural outgassing.

It is another object of the present invention to provide a process that reduces the level of VOCs without the oxidation that occurs during normal aging of components.

It is yet another object of the present invention to reduce the presence Of live mold, if any, in the subject vehicle.

SUMMARY OF THE INVENTION

The present invention is a process wherein an object or objects, especially habitable vehicles, are placed in a heated vacuum chamber. Outgassing rates are accelerated by applying heat to and reducing pressure (applying a vacuum) on the subject material. The process of the present invention maximizes the VOC outgassing rate of the materials in the subject objects, thereby reducing or eliminating the presence of VOCs when the objects are removed from the vacuum chamber.

At least one source of radiant heat is placed in the vacuum chamber. Heat sources may be placed either inside the object being treated, outside the object, or both. The process includes a means of measuring and monitoring the temperature of selected surfaces inside the object being treated. The heat sources are adjusted to maintain a temperature which is safe for the materials and which will promote maximum outgassing rates.

During the treatment process, while a vacuum and heat are being applied to the subject object, the gasses in the vacuum chamber are monitored for both their composition and quantity. When the outgassing rates of the VOCs reach acceptable levels, the process cycle is terminated. The vacuum in the chamber is broken to restore atmospheric pressure, and the object being treated is removed from the chamber.

An advantage of the present invention is that it reduces the outgassing rate of the materials from which a habitable vehicle is constructed to a level that is not harmful to humans in a drastically reduced period of time as compared to natural outgassing.

Another advantage of the present invention is that it can also reduce or eliminate the presence of live mold in the treated objects.

A still further advantage of the present invention is that the outgassing rates of the subject objects are reduced without the oxidation effect inherent in natural aging.

These and other objects and advantages of the present invention will become apparent to those skilled in the art in view of the description of the best presently known mode of carrying out the invention as described herein.

DETAILED DESCRIPTION OF THE INVENTION

The present invention is a process to reduce the levels of VOCs in an object to levels that are safe for human habitation. While the process may be used for building materials and the like, for purposes of description, the process will be defined with reference to habitable vehicles, specifically trailers. It is understood that the scope of the invention is not limited by the objects described as being treated by the process.

The process of the present invention applies a vacuum to the trailer. A vacuum chamber is constructed to receive the trailer. A trailer receiving end of the vacuum chamber is hinged to open to the side. While it will be recognized by those skilled in the art that any dimensions of the vacuum chamber that provide a volume sufficient to receive a trailer will suffice, in the preferred embodiment, the vacuum chamber has an outer diameter of 20 feet, with an 8" thick wall. The wall comprises a 0.5" thick outer shell of mild steel, a 0.125" to 0.188" thick inner shell of stainless steel, with expanding foam between the inner and outer shells. The vacuum chamber is typically cylindrical and approximately 40 ft. long. The chamber has an internal cross-section of approximately 274 sq. ft., and a minimum volume of approximately 12,500 cubic ft. The ends of the chamber are typically elliptical in cross section through the longitudinal axis of the chamber and are approximately 30 in. deep on the inside minor elliptical axis.

The vacuum chamber is most easily constructed of a plurality of sections. The joints between sections and at the entrance and exhaust of the chamber are closed with seal rings. The seal rings must transmit the weight of the sections to horizontal bases below them. The longitudinal expansion and contraction due to heat and vacuum forces on the vacuum chamber will be absorbed at each seal ring through flexure pivots somewhere between the seal ring and the horizontal base. A framework to load and support the trailer(s) during processing will consist of one framework inside each 8' long cylindrical section and is attached to the seal ring instead of the cylindrical section. There is a gap between one framework section and the next to prevent buckling during any longitudinal movement caused by expansion or contraction of the framework or of the cylindrical shells. The trailer framework load is transmitted to the seal plate, then to the flexure pivot, then to the base.

Once the trailer has been installed in the vacuum chamber, the chamber is sealed, and the vacuum pump is activated. As the pressure drops from atmospheric pressure (760 torr), the temperature in the vacuum chamber is raised via heating elements. The treatment temperature depends on the materials in the trailer being treated. The pressure in the vacuum chamber drops to 1-5 torr, and is held at that pressure until readings indicate that the outgassing rate is at acceptable levels. The processing cycle usually takes 18-24 hours.

During the processing cycle, mass spectrometry (MS), or a combination of gas chromatography and mass spectrometry (GC/MS), measurements are taken. These measurements provide dynamic, real time, feedback of the outgassing rates of the various VOC's in the vacuum chamber as a whole and in the living areas of the trailer in particular, the areas of greatest concern. The dynamic measurement of the gases present in the vacuum chamber provides information to the operator allowing him to make the appropriate adjustments in temperature and pressure, as well as determining the end of the treatment cycle.

At least one source of radiant heat is placed in the vacuum chamber. Heat sources may be placed either inside the object being treated, outside the object, or both. Process controls include a means of measuring and monitoring the temperature of selected surfaces inside the trailer being treated. The heat sources are adjusted to maintain a temperature that will not harm any of the materials in the trailer, but which will promote maximum outgassing rates. In the preferred embodiment, the temperature in the vacuum chamber during processing is approximately 115° F.

When the operator determines from the MS or GC/MS measurements that the outgassing rates of the VOCs have reached the desired levels, the process cycle is complete. The vacuum pump is turned off. At this point, the user of the system may choose to initiate an optional steam treatment. The vacuum chamber is then vented to atmospheric pressure so that the door may be opened.

The steam treatment is intended to be used for the treatment of mold in the trailers. The vacuum chamber is equipped with jets that introduce bleach laden steam into the vacuum chamber. As atmospheric pressure returns to the chamber, the bleach laden steam covers and is driven into any present mold. Another benefit from the steam treatment is the re-hydration of the surfaces subjected to the vacuum treatment, as the vacuum and heat combination will render the surface layers of objects in the trailer very dry. The steam quickly re-hydrates the dry surfaces.

The above disclosure is not intended as limiting. Those skilled in the art will readily observe that numerous modifications and alterations of the device may be made while retaining the teachings of the invention. Accordingly, the above disclosure should be construed as limited only by the restrictions of the appended claims.

I claim:

1. A process to accelerate outgassing of volatile organic compounds from objects comprising the following steps:
   constructing a vacuum chamber of sufficient size to contain the object;
   placing the object in the vacuum chamber;
   activating a vacuum pump to initiate a process cycle, the vacuum pump reducing the pressure in the vacuum chamber;
   applying heat to the object;
   applying steam with bleach included therein to the object;
   monitoring concentrations of the volatile organic compounds to determine when the process cycle is complete; and
   deactivating the vacuum pump and breaking a vacuum in the vacuum chamber so that the vacuum chamber returns to atmospheric pressure to complete the process cycle.

2. The process of claim 1, wherein the monitoring of concentrations of the volatile organic compounds to determine when the outgassing process is complete is accomplished via mass spectrometry or combined gas chromatography and mass spectrometry measurements.

3. The process of claim 1, wherein air pressure in the vacuum chamber is reduced to 1-5 torr during the process cycle.

4. The process of claim 1, wherein duration of the process cycle is 18-24 hours.

5. The process of claim 1, wherein a temperature in the vacuum chamber is raised to approximately 115° F.

6. The process of claim 1, wherein the vacuum chamber is approximately 40 ft. long with an internal cross-section of 274 sq. ft.

* * * * *